United States Patent [19]

Imaki et al.

[11] Patent Number: 4,590,319

[45] Date of Patent: May 20, 1986

[54] METHOD FOR THE PARTIAL HYDROGENATION OF CONJUGATED DIENES

[75] Inventors: Naoshi Imaki, Atsugi; Yoshiko Fukumoto, Yokohama, both of Japan

[73] Assignee: Mitsubishi Chemical Industries, Ltd., Tokyo, Japan

[21] Appl. No.: 705,526

[22] Filed: Feb. 26, 1985

[30] Foreign Application Priority Data

| Mar. 6, 1984 | [JP] | Japan | 59-42265 |
| Jun. 19, 1984 | [JP] | Japan | 59-126197 |
| Jun. 22, 1984 | [JP] | Japan | 59-128483 |
| Jan. 23, 1985 | [JP] | Japan | 60-10376 |
| Jan. 23, 1985 | [JP] | Japan | 60-10377 |
| Jan. 24, 1985 | [JP] | Japan | 60-11325 |
| Jan. 24, 1985 | [JP] | Japan | 60-11326 |
| Jan. 29, 1985 | [JP] | Japan | 60-15226 |

[51] Int. Cl.$^4$ .................................. C07C 5/05
[52] U.S. Cl. ........................ 585/274; 585/271
[58] Field of Search ........................ 585/274

[56] References Cited

U.S. PATENT DOCUMENTS 3,715,405  2/1973  Misono et al. ............... 585/274
3,937,745  2/1976  Wideman et al. ............ 585/274

FOREIGN PATENT DOCUMENTS 085326  7/1970  Japan ........................... 585/274
082684  7/1970  Japan ........................... 585/274
1407987  9/1972  United Kingdom .

OTHER PUBLICATIONS

Iwamoto, Masao, *Chemical Abstracts*, Dec. 7, 1970, vol. 73, No. 23, Abstract 1200496, pp. 329–330.
Kiyoshi Kawakami et al, *Chemistry Letters*, 1976, pp. 847–848.
Takuzo Funabiki et al, *Bulletin of the Chemical Society of Japan*, 1972, vol. 45, pp. 2723–2730.
Hiroshi Itatani et al, *Product R & D*, Selective Transition Metal Catalysts Complexed with Triphenyl Phosphine, 1972, vol. 11, No. 2, pp. 146–155.

*Primary Examiner*—Curtis R. Davis
*Attorney, Agent, or Firm*—Oblon, Fisher, Spivak, McClelland & Maier

[57] ABSTRACT

A method for the partial hydrogenation of conjugated dienes, characterized in that a chain conjugated diene in which the conjugated two double bonds have different numbers of substituents, is hydrogenated at a temperature of not higher than 50° C. in the presence of a catalyst composed essentially of (1) a cobalt compound, (2) an organophosphine compound and (3) an aluminum compound, to obtain a partially hydrogenated product wherein as between said conjugated two double bonds, the one having a greater number of substituents is selectively hydrogenated.

10 Claims, No Drawings

METHOD FOR THE PARTIAL HYDROGENATION OF CONJUGATED DIENES

The present invention relates to a method for the partial hydrogenation of conjugated dienes to produce olefin compounds, which are useful as starting materials for useful polymers and also as starting materials for various organic fine derivatives.

Various methods have been known for the hydrogenation of olefins having a plurality of double bonds, i.e. polyenes. In general, the hydrogenation tends to be difficult in the following order:
(1) Complete hydrogenation of all double bonds;
(2) Partial hydrogenation of any unspecified double bond
(for instance, non-selective partial hydrogenation from a diene to a monoene); and
(3) Selective partial hydrogenation (selective hydrogenation of a double bond at a specified position).

Further, it is known that among various methods for the selective partial hydrogenation (3), the difficulty increases in the following order:
(4) partial hydrogenation to form an internal olefin having thermodynamically improved stability;
(5) partial hydrogenation of the terminal double bond;
(6) partial hydrogenation of a double bond having a smaller number of substituents; and
(7) partial hydrogenation of a double bond having a greater number of substituents.

Heretofore, partial hydrogenation of isoprene has been known as an example of the partial hydrogenation corresponding to the above (7). The following methods have been known wherein isoprene is partially hydrogenated to obtain 3-methylbutene-1 in relatively good selectivity:

(a) a method wherein $Co(CN)_5{}^{3-}$ catalyst is used (Tarama et al., Bull. Chem. Soc. Jpn, 45, 2723 (1972));

(b) a method wherein $CoBr(PPh_3)_3$—$BF_3 \cdot OEt_2$ catalyst is used (Mizorogi et al., Chem. Lett., 847 (1976)); and (c) a method wherein $PdCl_2(PPh_3)_2$—$SnCl_2$ catalyst is used (Itatani et al., Ind. Eng. Chem. Prod. Res. Dev. 11, No. 2, 146 (1972)).

However, these methods are not yet adequately qualified for industrial application, since in the above methods (a) and (c), the selectivity for 3-methylbutene-1 is not sufficiently high, while in the method (b), the reaction rate and the catalytic activity are inadequate.

Further, there has been proposed a method wherein isoprene is partially hydrogenated in the presence of a catalyst composed of a cobalt compound-a phosphorus compound-an organoaluminum compound (Japanese Examined Patent Publication No. 22322/1970). However, in this method, the production rate of 3-methylbutene-1 is only 15% at best.

Yet, there has been drawback that even in a reaction system where the selectivity for 3-methylbutene-1 is relatively high among the above methods, if the conversion of isoprene becomes high, an isomerization reaction of the formed 3-methylbutene-1 is likely to take place rapidly, whereby the main product will be 2-methylbutene-2. This indicates that when the conversion of isoprene becomes high, the amount of isoprene in the system decreases, whereupon instead of isoprene, 3-methylbutene-1 will be coordinated on the catalyst, whereby the isomerization reaction of 3-methylbutene-1 to 2-methylbutene-2 will take place preferentially. On the other hand, it is believed that when the conversion of isoprene is low, isoprene exists in a great amount in the reaction system, whereby isoprene will be coordinated on the catalyst and the hydrogenation reaction of isoprene will take place preferentially.

There has been virtually no report on the selective partial hydrogenation of chain conjugated dienes, other than isoprene, in which the conjugated two double bonds have different numbers of substituents, wherein among the conjugated two double bonds, the one having a greater number of substituents is selectively hydrogenated.

Under the circumstances, the present inventors have conducted extensive researches to find a catalyst system and reaction conditions suitable for the selective partial hydrogenation of chain conjugated dienes with conjugated two double bonds having different numbers of substituents, whereby as between the conjugated two double bonds, the one having a greater number of substitutents is selectively hydrogenated. As a result, it has been found that such selective partial hydrogenation can be attained by conducting the hydrogenation reaction at a temperature of at most 50° C. by means of a catalyst system composed essentially of (1) a cobalt compound, (2) an organic phosphine compound and (3) an aluminum compound; that the selective partial hydrogenation can efficiently be conducted even when the hydrogenation reaction is conducted at a high conversion rate, if the cobalt compound and the phosphine compound are present in a certain specific ratio; that it is effective to use a boron halide compound and/or a proton acid having a pKa of at most 1 as an additional catalyst component; and further surprisingly that the presence of a specific α-olefin compound, cis-olefin compound or acetylene compound in the reaction system is effective. Thus, it is an object of the present invention to provide a method for producing, from a chain conjugated diene in which the conjugated two double bonds have different numbers of subsitutents, a partially hydrogenated product wherein as between the conjugated two double bonds, the one having a greater number of substitutents is selectively hydrogenated, as an olefin compound useful as a starting material for useful polymers or as a starting material for various organic fine derivatives.

In the broadest sense, the present invention provides a method for the partial hydrogenation of conjugated dienes, characterized in that a chain conjugated diene in which the conjugated two double bonds have different numbers of substituents, is hydrogenated at a temperature of not higher than 50° C. in the presence of a catalyst composed essentially of (1) a cobalt compound, (2) an organophosphine compound and (3) an aluminum compound, to obtain a partially hydrogenated product wherein as between said conjugated two double bonds, the one having a greater number of substituents is selectively hydrogenated.

Now, the present invention will be described in detail with reference to the preferred embodiments.

In the method of the present invention, a catalyst system is employed which is composed essentially of a cobalt compound, an organophosphine compound and an aluminum compound.

As the cobalt compound, there may be mentioned a salt such as cobalt chloride, cobalt sulfate, cobalt nitrate, cobalt carbonate, cobalt acetate, cobalt formate, cobalt naphthenate, cobalt oleate, cobalt octanoate, cobalt cyanide, cobalt fluoride, cobalt bromide or cobalt iodide; a chelate compound such as bis-(acetylacetonato)cobalt or tris(acetylacetonato)cobalt; or an organophosphorus complex compound such as chlorotris(triphenylphosphine)cobalt, bromotris(triphenylphosphine)cobalt, dichlorobis(triphenylphosphine)cobalt or dibromobis(triphenylphosphine)cobalt.

As the above-mentioned organophosphine compound, there may be mentioned a triarylphosphine such as triphenylphosphine, tris(p-methoxyphenyl)phosphine, tris(o-methoxyphenyl)phosphine, tris(p-trimethylsilylphenyl)phosphine, tri-p-tolylphosphine or tri-o-tolylphosphine; a trialkylphosphine such as tri-n-butylphosphine, tri-n-propylphosphine or tri-iso-propylphosphine; a triaralkylphosphine such as tribenzylphosphine; a mixed alkylarylphosphine such as diphenyl-n-propylphosphine, diphenyl-iso-propylphosphine, 1-diphenylphosphino-2-trimethylsilylethane or 1,2-bis-(diphenylphosphino)ethane; a triphenylphosphine cross-linked oligomer such as poly(diphenylphosphinostyrene); a diarylphosphinoaryl-substituted polysiloxane such as 1,1,2,2-tetramethyl-1,2-bis(p-diphenylphosphinophenyl)disiloxane, 1,1,2,2,3,3-hexamethyl-1,3-bis(p-diphenylphosphinophenyl)trisiloxane, 1,1,2,2,3,3,4,4-octamethyl-1,4-bis(p-diphenylphosphinophenyl)tetrasiloxane or 1,2,3,4-tetramethyl-1,2,3,4-tetrakis(p-diphenylphosphinophenyl)cyclotetrasiloxane; or a diarylphosphinoaryl-substituted polysilmethylene such as 1,2-bis(dimethyl-p-diphenylphosphinophenylsilyl)ethane.

As the above-mentioned aluminum compound, there may be mentioned an organoaluminum compound such as trimethylaluminum, triethylaluminum, tri-iso-butylaluminum, tri-n-butylaluminum, tri-n-propylaluminum, tri-n-hexylaluminum, diethylaluminumhydride, di-isobutylaluminum hydride, diethylaluminum chloride, di-isobutylaluminum chloride, diethylaluminum bromide, ethylaluminum dichloride, iso-butylaluminum dichloride, ethylaluminum dibromide, ethylaluminum sesquichloride, iso-butylaluminum sesquichloride or ethylaluminum sesquibromide; or an inorganic aluminum compound such as aluminum chloride or aluminum bromide.

As the aluminum compound, it is preferred to employ a combination of the above-mentioned organic aluminum compound and the inorganic aluminum compound, or a combination of a plurality of organic aluminum compounds. It is further preferred to employ a combination of an aluminum compound containing a halogen atom, i.e. an organic or inorganic aluminum compound containing a halogen atom, and an organic aluminum compound containing no halogen atom.

In the present invention, it is effective to use a boron halide compound and/or a proton acid having a pKa of at most 1 as an additional catalyst component.

As such boron halide compound, there may be mentioned boron trifluoride, boron trichloride, boron tribromide, boron trifluoride etherate (BF$_3$.OEt2) or a boron trifluoride-dimethanol compound (BF$_3$.2CH$_3$OH).

As the proton acid having a pKa of at most 1, there may be mentioned an inorganic proton acid such as sulfuric acid, hydrochloric acid, hydrobromic acid, nitric acid, phosphoric acid, perchloric acid, tetrafluoroboric acid or thiocyanic acid; or an organic proton acid such as trifluoroacetic acid, trichloroacetic acid, trichloromethane sulfonic acid, trifluoromethane sulfonic acid or p-toluene sulfonic acid. Among them, an organic proton acid is preferably used.

The above-mentioned cobalt compound is added usually in an amount of from 1 to 0.000001 mol, preferably from 0.1 to 0.00001 mol, as cobalt atoms, per mol of the starting material conjugated diene.

The above-mentioned organophosphine compound is added usually in an amount of at least 0.1 mol, preferably from 1 to 1000 mol, more preferably from 1 to 100 mol, especially from 1 to 20 mol, as phosphorus atoms, per mol of the cobalt atoms in the above cobalt compound, whereby it is possible to obtain a partially hydrogenated product wherein among the conjugated double bonds, the one having a greater number of substituents is selectively hydrogenated, in high selectivity, while maintaining a high conversion of the conjugated diene.

Further, when the above-mentioned organophosphine compound is added in an amount of more than 20 mol, preferably more than 20 mol and not more than 1000 mol, more preferably more than 20 mol and not more than 500 mol, it is possible to obtain a partially hydrogenated product in which among the conjugated double bonds, the one having a greater number of substituents is selectively hydrogenated, in high selectivity even if the conversion of the conjugated diene is increased to an extremely high level.

The above-mentioned aluminum compound is added usually in an amount of from 1 to 100 mol, preferably from 2 to 20 mol, as aluminum atoms, per mol of cobalt atoms in the above cobalt compound.

Further, in the case where a boron halide compound is used, it is added usually in an amount of from 1 to 100 mol, preferably from 1 to 10 mol, per mol of cobalt atoms in the cobalt compound. Likewise, in the case where a proton acid having a pKa of at most 1 is used, such a proton acid is added usually in an amount of from 1 to 100 mol, preferably from 1 to 10 mol, per mol of cobalt atoms in the cobalt compound.

The present invention is directed to hydrogenation wherein a chain conjugated diene in which the conjugated two double bonds have different numbers of substituents, is used, and among the conjugated two double bonds, the one having a greater number of substituents is selectively hydrogenated.

Here, the "chain" conjugated diene means a conjugated diene in which at least one of the conjugated two double bonds is in a chain portion. For instance, it includes a conjugated diene in which one of the double bonds is located in a cyclic portion and the other is located on a chain portion.

Specifically, there may be mentioned isoprene, 1-vinylcyclohexene, 1,3-pentadiene, 3-methyl-1,3-pentadiene, 1,3-hexadiene, 1,3-pentadiene, 5-methyl-1,3,6-heptatriene or myrcene.

When these conjugated dienes are hydrogenated by the method of the present invention, the double bond at the specific position as shown in Table A, i.e. the double bond having a greater number of substituents as between the conjugated two double bonds is selectively hydrogenated to give partially hydrogenated products.

TABLE A

| Conjugated dienes | Main products (partially hydrogenated products) |
|---|---|
| 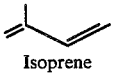 Isoprene | 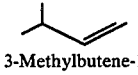 3-Methylbutene-1 |

TABLE A-continued

| Conjugated dienes | Main products (partially hydrogenated products) |
|---|---|
| 1-Vinylcyclohexene | Vinylcyclohexane |
| 1,3-Pentadiene | 1-Pentene |
| 3-Methyl-1,3-pentadiene | 3-Methyl-1-pentene |
| 1,3-Hexadiene | 1-Hexene |
| 5-Methyl-1,3,6-heptatriene | 3-Methyl-1,6-heptadiene |
| Myrcene | 3,7-Dimethyl-octa-1,6-diene |

In the present invention, it is effective to let a specific α-olefin compound, cis-olefin compound or acetylene compound be present in the reaction system in order to obtain a partially hydrogenated product in high selectivity wherein as between the conjugated two double bonds, the one having a greater number of substituents is selectively hydrogenated, even when the conversion of the conjugated diene is increased.

Such an α-olefin compound is represented by the formula:

where $R^1$ is an aryl group, a tertiary alkyl group or a tertiary silyl group, and $R^2$ is a hydrogen atom, an alkyl group, a tertiary silyl group or an aryl group. Specifically, there may be mentioned styrene, α-methylstyrene, vinylnaphthalene, 1,1-diphenylethylene, 3,3-dimethylbutene-1, adamantylethylene, vinyltrimethylsilane or 1,1-bis(trimethylsilyl)ethylene.

As the cis-olefin compound, it is preferred to use a compound represented by the formula:

where each of $R^1$ and $R^2$ is an alkyl group, a silyl group or an aryl group, or $R^1$ and $R^2$ may together form a ring. Particularly preferred among them, are cis-olefins wherein $R^1$ and $R^2$ are linked to form a bridged olefin compound and the carbon atoms adjacent to the olefin portion are bridge head carbon atoms, and cis-olefins wherein each of $R^1$ and $R^2$ is a tertiary alkyl group, a tertiary silyl group or an aryl group. Specifically, there may be mentioned a bridged olefin such as 2-norbornene, 2,5-norbornadiene, dicyclopentadiene, bicyclo[2,2,2]octa-2-ene, bicyclo[2,2,2]octa-2,5,7-triene, bicylo[2,1,1]hexa-2-ene or bicyclo[2,2,0]hexa-2,5-diene; a cis-tertiary alkyl substituted olefin such as cis-di-t-butylethylene; a cis-tertiary silyl substituted olefin such as cis-bis(trimethylsilyl)ethylene; and a cis-aryl-substituted olefin such as cis-stilbene or cis-1,2-dinaphthylethylene.

As the above-mentioned acetylene compound, there may be specifically mentioned a straight chain acetylene hydrocarbon such as acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 3-decyne or 4-decyne; an alkyl acetylene such as 3,3-dimethylbutyne-1 or 2,2,5,5-tetramethylhexyne-3; an aryl acetylene such as phenyl acetylene or diphenylacetylene; and a silyl acetylene such as trimethylsilyl acetylene or bis(trimethylsilyl)acetylene.

The above-mentioned α-olefin compound, cis-olefin compound or acetylene compound is added usually in an amount of from 1 to 100 mol, preferably from 3 to 20 mol, per mol of cobalt atoms in the cobalt compound.

The reason why the partially hydrogenated product of the present invention is obtainable in high selectivity even when the conversion of the conjugated diene is increased, by incorporating the above-mentioned specific α-olefin compound, cis-olefin compound or acetylene compound in the reaction system, is not necessarily clear. However, it is believed that each of these compounds acts competitively with the partially hydrogenated product, as a compound which has weaker coordinating power to the catalyst than the starting material conjugated diene but stronger coordinating power than the partially hydrogenated product, whereby the coordination of the partially hydrogenated product to the catalyst is prevented in the case where the conversion of the conjugated diene is high.

The reaction is usually conducted at a temperature of at most 50° C. If the temperature is higher than 50° C., the production rate of isomers other than the desired product tends to increase. The reaction temperature is preferably from −20° to 50° C., more preferably from −5° to 45° C.

As the reaction pressure, a pressure from atmospheric pressure to 100 kg/cm² is usually employed.

The reaction is conducted usually in the presence of a solvent. As such a solvent, any inert solvent may be employed. For instance, there may be employed an aromatic hydrocarbon such as toluene, or a halogenated aromatic hydrocarbon such as chlorobenzene, dichlorobenzene, trichlorobenzene or bromobenzene.

The reaction may be conducted in any manner of a batch system, a semicontinuous system or a continuous system. The reaction product may be isolated by a usual separation method such as distillation, extraction or adsorption. When the separation is conducted by distillation, the distillation residue may be recycled for reuse as the catalyst solution.

Now, the present invention will be described in detail with reference to Examples. However, it should be understood that the present invention is by no means restricted by these specific Examples.

The following abbreviations were used, and the conversion and the production rate were calculated in accordance with the following equations.

IP:Isoprene
3MB1:3-Methylbutene-1
2MB1:2-Methylbutene-1
2MB2:2-Methylbutene-2
2MB:2-Methylbutane $$\text{Conversion (\%) of conjugated diene} = \frac{\text{charged conjugated diene (mols)} - \text{Recovered conjugated diene (mols)}}{\text{Charged conjugated diene (mols)}} \times 100$$

$$\text{Production ratio (\%)} = \frac{\text{Each hydrogenated product (mols)}}{\text{Sum of all hydrogenated products (mols)}} \times 100$$

EXAMPLE 1

Into a flask having a capacity of 100 ml, 51 mg (0.2 mmol) of cobalt (II) acetylacetonate and 157 mg (0.6 mmol) of triphenylphosphine were charged, and after thoroughly flushing the interior of the flask with nitrogen, 20 ml of chlorobenzene was added as a solvent. To the suspension solution of chlorobenzene, 0.35 ml (0.4 mmol) of a toluene solution containing 15% by weight of triethylaluminum was dropwise added under stirring and cooling with ice water. Further, 44 mg (0.33 mmol) of aluminum chloride powder was added, and finally 0.3 ml (3.0 mmol) of isoprene was added. The interior of the system was flushed with hydrogen, and then hydrogen was supplied under atmospheric pressure while vigorously stirring the mixture under cooling with ice water. After the introduction of hydrogen, absorption of hydrogen started, and about 5 minutes later, absorption of a substantially theoretical amount of hydrogen was observed, and the reaction was terminated. The reaction solution was analyzed by gas chromatography, whereby the following results were obtained.

| IP   | Conversion       | 95%  |
|------|------------------|------|
| 3MB1 | Production ratio | 83%  |
| 2MB1 | "                | 4%   |
| 2MB2 | "                | 12%  |
| 2MB  | "                | 0.1% |

COMPARATIVE EXAMPLE 1

Into a flask having a capacity of 100 ml, 185 mg (0.2 mmol) of bromotris(triphenylphosphine)cobalt (I) complex was charged, and after thoroughly flushing the interior of the flask with nitrogen, 20 ml of bromobenzene was added as a solvent. To the bromobenzene solution, 55 μl (0.44 mmol) of borontrifluoride etherate was dropwise added under stirring and cooling with ice water. Finally, 0.3 ml (3.0 mmol) of isoprene was added, and after flushing the interior of the system with hydrogen, hydrogen was introduced under atmospheric pressure while vigorously stirring and cooling with ice water to conduct the hydrogenation reaction of isoprene. It took 30 minutes for the absorption of a theoretical amount of hydrogen. The reaction solution was analyzed by gas chromatography, whereby the conversion of IP was 90%.

EXAMPLE 2

The reaction was conducted in the same manner as in Example 1 except that 26 mg (0.2 mmol) of cobalt (II) chloride was used instead of cobalt (II) acetylacetonate, 0.66 ml (0.4 mmol) of a toluene solution containing 13.7% by weight of triisobutylaluminum was used instead of triethylaluminum, and 53 mg (0.4 mmol) of aluminum chloride was employed. About 15 minutes later, absorption of a substantially theoretical amount of hydrogen was observed. The reaction solution was analyzed by gas chromatography, whereby the following results were obtained.

| IP   | Conversion       | 97% |
|------|------------------|-----|
| 3MB1 | Production ratio | 85% |
| 2MB1 | "                | 4%  |
| 2MB2 | "                | 11% |

EXAMPLE 3

The reaction was conducted in the same manner as in Example 1 except that 71 mg (0.2 mmol) of cobalt (III) acetylacetonate was used instead of cobalt (II) acetylacetonate, 0.53 ml (0.6 mmol) of a toluene solution containing 15% by weight of triethylaluminum and 55 mg (0.41 mmol) of aluminum chloride were employed, and the vigorous stirring was conducted for about 6 hours under cooling with ice water. The reaction solution was analyzed by gas chromatography, whereby the following results were obtained.

| IP   | Conversion       | 79% |
|------|------------------|-----|
| 3MB1 | Production ratio | 83% |
| 2MB1 | "                | 5%  |
| 2MB2 | "                | 12% |

EXAMPLE 4

The reaction was conducted in the same manner as in Example 1 except that 182 mg (0.6 mmol) of tri-p-tolylphosphine was used instead of triphenylphosphine, and 0.66 ml (0.4 mmol) of a toluene solution containing 13.7% by weight of triisobutylaluminum was used instead of the toluene solution of triethylaluminum. About 3 minutes later, absorption of a substantially theoretical amount of hydrogen was observed. The reaction solution was analyzed by gas chromatography, whereby the following results were obtained.

| IP   | Conversion       | 97% |
|------|------------------|-----|
| 3MB1 | Production ratio | 86% |
| 2MB1 | "                | 4%  |
| 2MB2 | "                | 10% |

EXAMPLE 5

The reaction was conducted in the same manner as in Example 1 except that 211 mg (0.6 mmol) of tris(p-methoxyphenyl)phosphine was used instead of triphenylphosphine, 0.66 ml (0.4 mmol) of a toluene solution containing 13.7% by weight of triisobutylaluminum was used instead of the toluene solution of triethylaluminum, and 53 mg (0.4 mmol) of aluminum chloride powder was employed. About 3 minutes later, absorption of a substantially theoretical amount of hydrogen was observed. The reaction solution was analyzed by gas chromatography, whereby the following results were obtained.

| IP | Conversion | 97% |
|----|------------|-----|

-continued

| | | |
|---|---|---|
| 3MB1 | Production ratio | 89% |
| 2MB1 | " | 2% |
| 2MB2 | " | 9% |

EXAMPLE 6

The reaction was conducted in the same manner as in Example 1 except that 45 mg (0.18 mmol) of cobalt (II) acetylacetonate was used, 253 mg (0.54 mmol) of tris(p-trimethylsilylphenyl)phosphine was used instead of triphenylphosphine, and 0.60 ml (0.36 mmol) of a toluene solution containing 13.7% by weight of triisobutylaluminum was used instead of the toluene solution of triethylaluminum. About 4 minutes later, absorption of a substantially theoretical amount of hydrogen was observed. The reaction solution was analyzed by gas chromatography, whereby the following results were obtained.

| | | |
|---|---|---|
| IP | Conversion | 96% |
| 3MB1 | Production ratio | 81% |
| 2MB1 | " | 7% |
| 2MB2 | " | 12% |

EXAMPLES 7 TO 12

The reaction was conducted in the same manner as in Example 1 except that an aluminum compound as identified in Table 1 was used in an amount as identified in Table 1. The reaction solution was analyzed by gas chromatography, whereby the results as shown in Table 1 were obtained.

TABLE 1

| Example No. | Aluminum compound** Amount (mmol) | Reaction Time (min.) | Conversion of IP (%) | Production ratio (%) | | | |
|---|---|---|---|---|---|---|---|
| | | | | 3MB1 | 2MB1 | 2MB2 | 2MB |
| 7 | i-Bu$_3$Al/AlCl$_3$ 0.4      0.47 | 2.5 | 89 | 83 | 6 | 11 | 0 |
| 8 | i-Bu$_2$AlH/AlCl$_3$ 0.4      0.39 | 3 | 91 | 82 | 6 | 12 | 0 |
| 9 | Et$_3$Al/EtAlCl$_2$ 0.4      0.2 | 10 | 88 | 82 | 4 | 14 | 0 |
| 10 | Et$_3$Al/Et$_3$Al$_2$Cl$_3$ 0.4      0.3 | 6.5 | 88 | 80 | 4 | 16 | 0 |
| 11 | Et$_3$Al 0.8 | 5.5 | 48 | 81 | 6 | 12 | 0.8 |
| 12 | Et$_2$AlCl 0.7 | 15 | 89 | 83 | 4 | 13 | 0 |

**i-Bu$_3$Al: tri-iso-butylaluminum, i-Bu$_2$AlH: di-iso-butylaluminum hydride, Et$_3$Al: triethylaluminum, EtAlCl$_2$: ethyldichloroaluminum, Et$_3$Al$_2$Cl$_3$: ethylaluminum sesquichloride, Et$_2$AlCl: diethylchloroaluminum. They were used in their toluene solutions having concentrations of 13.7, 13.5, 15.0, 16.1, 14.1 and 14.8% by weight, respectively.

EXAMPLE 13

The reaction was conducted in the same manner as in Example 1 for 200 minutes except that the amount of isoprene was changed to 4.0 ml (40 mmol) and the amount of chlorobenzene was changed to 10 ml. The reaction solution was analyzed by gas chromatography, whereby the following results were obtained.

| | | |
|---|---|---|
| IP | Conversion | 88% |
| 3MB1 | Production ratio | 84% |
| 2MB1 | " | 4% |
| 2MB2 | " | 12% |

Further, the production ratio of 3MB1 relative to cobalt atoms in the catalyst was 147 mol/mol-Co.

EXAMPLE 14

The reaction was conducted in the same manner as in Example 1. After the completion of the reaction, the products and feed isoprene were distilled off under reduced pressure by means of a vacuum pump, and under a refreshed, hydrogen atmosphere, 0.3 ml (3.0 mmol) of isoprene was added and the reaction was repeated in the same manner as in Example 1. In the fourth repetition, the absorption rate of hydrogen decreased to a level of about a half of the absorption rate in the first operation, and the reaction time required was 10 minutes. The reaction solution after repeating the reaction four times was analyzed by gas chromatography, whereby the following results were obtained.

| | | |
|---|---|---|
| IP | Conversion | 79% |
| 3MB1 | Production ratio | 84% |
| 2MB1 | " | 5% |
| 2MB2 | " | 11% |

EXAMPLE 15

The hydrogenation reaction of Example 1 was conducted at room temperature (18° C.). About 3 minutes later, absorption of a substantially theoretical amount of hydrogen was observed. The reaction solution was analyzed by gas chromatography, whereby the following results were obtained.

| | | |
|---|---|---|
| IP | Conversion | 93% |
| 3MB1 | Production ratio | 80% |
| 2MB1 | " | 5% |
| 2MB2 | " | 15% |

EXAMPLE 16

The hydrogenation reaction of Example 1 was conducted in a dry ice-carbontetrachloride bath. About 6 minutes later, absorption of a substantially theoretical amount of hydrogen was observed. The reaction solution was analyzed by gas chromatography, whereby the following results were obtained.

| | | |
|---|---|---|
| IP | Conversion | 91% |
| 3MB1 | Production ratio | 85% |
| 2MB1 | " | 4% |
| 2MB2 | " | 11% |

COMPARATIVE EXAMPLE 2

The hydrogenation reaction of Example 1 was conducted under atmospheric pressure for 3 hours in an oil bath at 65° C. with a dry ice trap provided between the hydrogen inlet and the reactor. The reaction solution was analyzed by gas chromatography, whereby the following results were obtained.

| IP | Conversion | 95% |
|---|---|---|
| 3MB1 | Production ratio | 19% |
| 2MB1 | " | 22% |
| 2MB2 | " | 58% |
| 2MB | " | 0.9% |

EXAMPLE 17

Into a flask having a capacity of 100 ml, 51 mg (0.2 mmol) of cobalt (II) acetylacetonate and 157 mg (0.6 mmol) of triphenylphosphine were charged, and after thoroughly flushing the interior of the flask with nitrogen, 20 ml of chlorobenzene was added as a solvent. To the suspension solution of chlorobenzene, 0.35 ml (0.4 mmol) of a toluene solution containing 15% by weight of triethylaluminum was dropwise added under stirring and cooling with ice water. Further, 55 µl (0.44 mmol) of boron trifluoride etherate was added thereto. Finally, 0.3 ml (3.0 mmol) of isoprene was added, and after flushing the interior of the system with hydrogen, hydrogen was introduced under atmospheric pressure while vigorously stirring and cooling with ice water. After the initiation of the introduction of hydrogen, absorption of hydrogen started. About 4.5 minutes later, absorption of a substantially theoretical amount of hydrogen was observed. Then, the reaction was terminated, and the reaction solution was analyzed by gas chromatography, whereby the following results were obtained.

| IP | Conversion | 87% |
|---|---|---|
| 3MB1 | Production ratio | 85% |
| 2MB1 | " | 3.8% |
| 2MB2 | " | 11% |
| 2MB | " | 0.9% |

COMPARATIVE EXAMPLE 3

Into a flask having a capacity of 100 ml, 176 mg (0.2 mmol) of chlorotris(triphenylphosphine) cobalt (I) complex was charged, and after thoroughly flushing the interior of the flask with nitrogen, 20 ml of chlorobenzene was added as a solvent. To the chlorobenzene solution, 55 µl (0.44 mmol) of boron trifluoride etherate was dropwise added under stirring and cooling with ice water. Finally, 0.3 ml (3.0 mmol) of isoprene was added, and after flushing the inteior of the system with hydrogen, hydrogen was introduced under atmospheric pressure while vigorously stirring and cooling with ice water to conduct the hydrogenation reaction. It took about 10 minutes until a substantially theoretically amount of hydrogen was absorbed. The reaction solution was analyzed by gas chromatography, whereby the following results were obtained.

| IP | Conversion | 81% |
|---|---|---|
| 3MB1 | Production ratio | 86% |
| 2MB1 | " | 4% |
| 2MB2 | " | 10% |
| 2MB | " | 0% |

EXAMPLE 18

Into a flask having a capacity of 100 ml, 51 mg (0.2 mmol) of cobalt (II) acetylacetonate and 157 mg (0.6 mmol) of triphenylphosphine were charged, and after thoroughly flushing the interior of the flask with nitrogen, 20 ml of chlorobenzene was added as a solvent. To the suspension solution of chlorobenzene, 0.35 ml (0.4 mmol) of a toluene solution containing 15% by weight of triethylaluminum was dropwise added while stirring and cooling with ice water. Further, 49 mg (0.3 mmol) of trichloroacetic acid was added, and finally 0.3 ml (3.0 mmol) of isoprene was added. After flushing the interior of the system with hydrogen, hydrogen was introduced under atmospheric pressure while vigorously stirring and cooling with ice water. After the initiation of the introduction of hydrogen, absorption of hydrogen started. About 4.5 minutes later, absorption of a substantially theoretical amount of hydrogen was observed. Then, the reaction was terminated, and the reaction solution was analyzed by gas chromatography, whereby the following results were obtained.

| IP | Conversion | 93% |
|---|---|---|
| 3MB1 | Production ratio | 82% |
| 2MB1 | " | 4% |
| 2MB2 | " | 14% |

EXAMPLE 19

The reaction was conducted in the same manner as in Example 18 except that 50 mg (0.33 mmol) of trifluoromethanesulfonic acid was used instead of trichloroacetic acid. About 18 minutes later, absorption of a substantially theoretical amount of hydrogen was observed. Then, reaction was terminated, and the reaction solution was analyzed by gas chromatography, whereby the following results were obtained.

| IP | Conversion | 91% |
|---|---|---|
| 3MB1 | Production ratio | 89.5% |
| 2MB1 | " | 1.4% |
| 2MB2 | " | 9% |
| 2MB | " | 0.1% |

EXAMPLE 20

Into a flask having a capacity of 100 ml, 59 mg (0.2 mmol) of cobalt (II) acetylacetonate dihydrate and 157 mg (0.6 mmol) of triphenylphosphine were charged, and after thoroughly flushing the interior of the flask with nitrogen, 20 ml of chlorobenzene was added. To the chlorobenzene solution, 0.42 ml (0.46 mmol) of a toluene solution containing 14.5% by weight of triethylaluminum was dropwise added while stirring and cooling with ice water. Further, 0.52 ml (0.34 mmol) of a toluene solution containing 18.4% by weight of ethylaluminum sesquichloride was dropwise added. Finally, 0.3 ml (3.0 mmol) of isoprene was added, and after flushing the interior of the system with hydrogen, hydrogen was introduced under atmospheric pressure while vigorously stirring and cooling with ice water.

After the initiation of the introduction of hydrogen, absorption of hydrogen started, and the hydrogenation reaction proceeded. When the absorption of hydrogen reached about 90% of the theoretical amount, the reaction solution was analyzed by gas chromatography, whereby the conversion of IP was found to be 90%, and the production ratio of 3MB1 was 82%. The hydrogenation reaction was further continued, and the reaction solution was again analyzed when absorption of a substantially theoretical amount of hydrogen was observed, whereby the conversion of IP was found to be 98%, but the production ratio of 3MB1 was as little as 0.4%, and the production ratio of 2MB2 increased to 87.9%. The production ratios of the reduction products other than 3MB1 and 2MB2, were 7.6% of 2MB1 and 4.1% of 2MB.

EXAMPLE 21

The reaction was conducted in the same manner as in Example 20 except that the amount of triphenylphosphine was increased to 1.31 g (5 mmol).

When the conversion of IP reached 90%, the reaction solution was analyzed by gas chromatography, whereby the production ratio of 3MB1 was 82% as in the case of Example 20. The reaction was further continued to increase the conversion of IP, and when absorption of a substantially theoretical amount of hydrogen was observed, the reaction solution was analyzed, whereby the conversion of IP was 99.4%, and the production ratio of 3MB1 was 82%. The production ratios of other reduction products were 4.6% of 2MB1, 13.8% of 2MB2 and 0.1% of 2MB.

EXAMPLE 22

The reaction was conducted in the same manner as in Example 21 except that the amount of triphenylphosphine was changed to 2.62 g (10 mmol), 0.60 ml (0.46 mmol) of a toluene solution containing 10.0% by weight of triethylaluminum was used as the toluene solution of triethylaluminum, and 0.96 ml (0.34 mmol) of a toluene solution containing 10.0% by weight of ethylaluminum sesquichloride was used as the toluene solution of ethylaluminum sesquichloride. The reaction was terminated when absorption of a substantially theoretical amount of hydrogen was observed, and the reaction solution was analyzed by gas chromatography, whereby the following results were obtained.

| IP | Conversion | 98.1% |
|---|---|---|
| 3MB1 | Production ratio | 78.4% |
| 2MB1 | " | 6.4% |
| 2MB2 | " | 15.1% |
| 2MB | " | 0.1% |

EXAMPLE 23

The reaction was conducted in the same manner as in Example 21 except that 0.60 ml (0.46 mmol) of a toluene solution containing 10.0% by weight of triethylalumimum was used instead of the toluene solution of triethylaluminum, and 52 mg (0.39 mmol) of aluminum chloride was added instead of the toluene solution of ethylaluminum sesquichloride. The reaction was terminated when absorption of a substantially theoretical amount of hydrogen was observed, and the reaction solution was analyzed by gas chromatography, whereby the following results were obtained.

| IP | Conversion | 96.8% |
|---|---|---|
| 3MB1 | Production ratio | 83.8% |
| 2MB1 | " | 4.8% |
| 2MB2 | " | 11.3% |
| 2MB | " | 0.1% |

EXAMPLE 24

The reaction was conducted in the same manner as in Example 21 except that a flask having a capacity of 1 liter was used, the amount of cobalt (II) acetylacetonate dihydrate was changed to 1.47 g (5.0 mmol), the amount of triphenylphosphine was changed to 32.75 g (125 mmol), the amount of chlorobenzene was changed to 250 ml, 15.1 ml (11.4 mmol) of a toluene solution containing 10.0% by weight of triethylaluminum was used as the toluene solution of triethylaluminum, 15.5 ml (8.55 mmol) of a toluene solution containing 15.3% by weight of ethylaluminum sesquichloride was used as the toluene solution of ethylaluminun sesquichloride, and the amount of isoprene was changed to 100 ml (1.0 mol). The reaction was terminated when absorption of a substantially theoretical amount of hydrogen was observed, and the reaction solution was analyzed by gas chromatography, whereby the following results were obtained.

| IP | Conversion | 99.9% |
|---|---|---|
| 3MB1 | Production ratio | 77.8% |
| 2MB1 | " | 4.2% |
| 2MB2 | " | 17.9% |
| 2MB | " | 0.1% |

EXAMPLE 25

The reaction was conducted in the same manner as in Example 20 except that after an addition of 0.60 ml (0.46 mmol) of a toluene solution containing 10.0% by weight of triethylaluninum as the toluene solution of triethylaluminum 55 μl (0.44 mmol) of boron trifluoride etherate was added without using the toluene solution of ethylaluminum sesquichloride, and then isoprene was added. The reaction solution was analyzed when the absorption of hydrogen reached about 85% of the theoretical amount, whereby the conversion of IP was 85% and the production ratio of 3MB1 was 85%. Further, the reaction was continued to increase the conversion of IP, and when absorption of a substantially theoretical amount of hydrogen was observed, the reaction solution was analyzed, whereby the following results were obtained.

| IP | Conversion | 92% |
|---|---|---|
| 3MB1 | Production ratio | 0.5% |
| 2MB1 | " | 6.8% |
| 2MB2 | " | 89% |
| 2MB | " | 3.2% |

EXAMPLE 26

The reaction was conducted in the same manner as in Example 25 except that the amount of triphenylphosphine was increased to 1.31 g (5.0 mmol). When the conversion of IP was 85%, the production ratio of 3MB1 was 85% as in the case of Example 25. The conversion of IP was further increased, and when absorption of a substantially theoretical amount of hydrogen was observed, the reaction solution was analyzed, whereby the following results were obtained.

| IP   | Conversion       | 92%  |
|------|------------------|------|
| 3MB1 | Production ratio | 44%  |
| 2MB1 | "                | 6.4% |
| 2MB2 | "                | 48%  |
| 2MB  | "                | 1.6% |

EXAMPLE 27

The reaction was conducted in the same manner as in Example 25 except that 50 mg (0.33 mmol) of trifluoromethanesulfonic acid was employed instead of boron trifluoride etherate. When absorption of hydrogen reached about 90% of the theoretical amount, the reaction solution was analyzed, whereby the conversion of IP was 90%, and the production ratio of 3MB1 was 89.4%. The conversion of IP was further increased, and when absorption of a substantially theoretical amount of hydrogen was observed, the reaction solution was analyzed, whereby the following results were obtained.

| IP   | Conversion       | 99%  |
|------|------------------|------|
| 3MB1 | Production ratio | 0.4% |
| 2MB1 | "                | 8%   |
| 2MB2 | "                | 88%  |
| 2MB  | "                | 3.6% |

EXAMPLE 28

The reaction was conducted in the same manner as in Example 27 except that the amount of triphenylphosphine was increased to 1.31 g (5.0 mmol). When the conversion of IP was 90%, the production ratio of 3MB1 was 89.4% as in the case of Example 27. The conversion of IP was further increased, and when absorption of a substantially theoretical amount of hydrogen was observed, the reaction solution was analyzed, whereby the following results were obtained.

| IP   | Conversion       | 99.2% |
|------|------------------|-------|
| 3MB1 | Production ratio | 56%   |
| 2MB1 | "                | 11%   |
| 2MB2 | "                | 31%   |
| 2MB  | "                | 2%    |

EXAMPLE 29

The reaction was conducted in the same manner as in Example 20 except that 0.60 ml (0.46 mmol) of a toluene solution containing 10.0% by weight of triethylaluminum was used as the toluene solution of triethylaluminum, 0.96 ml (0.34 mmol) of a toluene solution containing 10.0% by weight of ethylaluminum sesquichloride was used as the toluene solution of ethylaluminum sesquichloride, and after the addition of isoprene, 0.21 ml (1.6 mmol) of α-methylstyrene was added. When the absorption of hydrogen reached about 90% of the theoretical amount, the reaction solution was analyzed, whereby the conversion of IP was 90%, and the production ratio of 3MB1 was 82%. The conversion of IP was further increased, and when absorption of a substantially theoretical amount of hydrogen was observed, the reaction solution was analyzed, whereby the following results were obtained.

| IP   | Conversion       | 95%  |
|------|------------------|------|
| 3MB1 | Production ratio | 49%  |
| 3MB2 | "                | 6.5% |
| 2MB2 | "                | 43%  |
| 2MB  | "                | 1.5% |

EXAMPLE 30

The reaction was conducted in the same manner as in Example 29 except that 0.18 ml (1.6 mmol) of styrene was used instead of α-methylstyrene. When the absorption of hydrogen reached about 90% of the theoretical amount, the reaction solution was analyzed, whereby the conversion of IP was 90%, and the production ratio of 3MB1 was 80%. The conversion of IP was further increased, and when absorption of a substantially theoretical amount of hydrogen was observed, the reaction solution was analyzed, whereby the following results were obtained.

| IP   | Conversion       | 95%  |
|------|------------------|------|
| 3MB1 | Production ratio | 79%  |
| 2MB1 | "                | 4.6% |
| 2MB2 | "                | 16%  |
| 2MB  | "                | 0.4% |

EXAMPLE 31

The reaction was conducted in the same manner as in Example 29 except that 0.25 ml (1.6 mmol) of trimethylvinylsilane was used instead of α-methylstyrene. When the absorption of hydrogen reached about 90% of the theoretical amount, the reaction solution was analyzed, whereby the conversion of IP was 90%, and the production ratio of 3MB1 was 82%. The conversion of IP was further increased, and when absorption of a substantially theoretical amount of hydrogen was observed, the reaction solution was analyzed, whereby the following results were obtained.

| IP   | Conversion       | 96%  |
|------|------------------|------|
| 3MB1 | Production ratio | 47%  |
| 2MB1 | "                | 4.7% |
| 2MB2 | "                | 48%  |
| 2MB  | "                | 0.3% |

EXAMPLE 32

The reaction was conducted in the same manner as in Example 29 except that 0.21 ml (1.6 mmol) of 3,3-dimethylbutene-1 was used instead of α-methylstyrene. When the absorption of hydrogen reached about 90% of the theoretical amount, the conversion of IP was 90%, and the production ratio of 3MB1 was 80%. The conversion of IP was further increased, and when absorption of a substantially theoretical amount of hydrogen was observed, the reaction solution was analyzed, whereby the following results were obtained.

| IP   | Conversion       | 98%  |
|------|------------------|------|
| 3MB1 | Production ratio | 32%  |
| 2MB1 | "                | 40%  |
| 2MB2 | "                | 27%  |
| 2MB  | "                | 0.7% |

EXAMPLE 33

The reaction was conducted in the same manner as in Example 29 except that 0.22 ml (1.6 mmol) of vinylcyclohexane was used instead of α-methylstyrene. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 95% |
|---|---|---|
| 3MB1 | Production ratio | 0.2% |
| 2MB1 | " | 7.8% |
| 2MB2 | " | 89% |
| 2MB | " | 3% |

EXAMPLE 34

The reaction was conducted in the same manner as in Example 20 except that 0.60 ml (0.46 mmol) of a toluene solution containing 10.0% by weight of triethylaluminum was used as the toluene solution of triethylaluminum, 0.96 ml (0.34 mmol) of a toluene solution containing 10.0% by weight of ethylaluminum sesquichloride was used as the toluene solution of ethylaluminum sesquichloride, and after the addition of isoprene, 151 mg (1.6 mmol) of 2-norbornene was added. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 97% |
|---|---|---|
| 3MB1 | Production ratio | 81% |
| 2MB1 | " | 5.8% |
| 2MB2 | " | 13% |
| 2MB | " | 0.2% |

EXAMPLE 35

The reaction was conducted in the same manner as in Example 34 except that 0.11 ml (0.8 mmol) of dicyclopentadiene was used instead of 2-norbornene. When the absorption of hydrogen reached about 90% of the theoretical amount, the reaction solution was analyzed, whereby the conversion of IP was 90%, and the production ratio of 3MB1 was 79%. The conversion of IP was further increased, and when absorption of a substantially theoretical amount of hydrogen was observed, the reaction solution was analyzed, whereby the following results were obtained.

| IP | Conversion | 97% |
|---|---|---|
| 3MB1 | Production ratio | 78% |
| 2MB1 | " | 4.7% |
| 2MB2 | " | 17% |
| 2MB | " | 0.3% |

EXAMPLE 36

The reaction was conducted in the same manner as in Example 34 except that 0.08 ml (0.8 mmol) of 2,5-norbornadiene was used instead of 2-norbornene. When the absorption of hydrogen reached about 90% of the theoretical amount, the reaction solution was analyzed, whereby the conversion of IP was 90%, and the production ratio of 3MB1 was 82%. The conversion of IP was further increased, and when absorption of a substantially theoretical amount of hydrogen was observed, the reaction solution was analyzed, whereby the following results were obtained.

| IP | Conversion | 95% |
|---|---|---|
| 3MB1 | Production ratio | 54% |
| 2MB1 | " | 6.5% |
| 2MB2 | " | 38% |
| 2MB | " | 1.5% |

EXAMPLE 37

The reaction was conducted in the same manner as in Example 34 except that 0.28 ml (1.6 mmol) of cis-stilbene was used instead of 2-norbornene. When the absorption of hydrogen reached about 90% of the theoretical amount, the reaction solution was analyzed, whereby the conversion of IP was 90%, and the production ratio of 3MB1 was 82%. The conversion of IP was further increased, and when absorption of a substantially theoretical amount of hydrogen was observed, the reaction solution was analyzed, whereby the following results were obtained.

| IP | Conversion | 96% |
|---|---|---|
| 3MB1 | Production ratio | 58% |
| 2MB1 | " | 6.6% |
| 2MB2 | " | 35% |
| 2MB | " | 0.4% |

EXAMPLE 38

The reaction was conducted in the same manner as in Example 34 except that 288 mg (1.6 mmol) of trans-stilbene was used instead of 2-norbornene. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 95% |
|---|---|---|
| 3MB1 | Production ratio | 0.2% |
| 2MB1 | " | 7% |
| 2MB2 | " | 90% |
| 2MB | " | 2.5% |

EXAMPLE 39

The reaction was conducted in the same manner as in Example 20 except that 0.60 ml (0.46 mmol) of a toluene solution containing 10.0% by weight of triethylaluminum was used as the toluene solution of triethylaluminum, 0.96 ml (0.34 mmol) of a toluene solution containing 10.0% by weight of ethylaluminum sesquichloride was used as the toluene solution of ethylaluminum sesquichloride, and after the addition of isoprene, 0.18 ml (1.6 mmol) of 3-hexyne was added. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 93% |
|---|---|---|
| 3MB1 | Production ratio | 81% |
| 2MB1 | " | 3.6% |
| 2MB2 | " | 15% |
| 2MB | " | 0.3% |

EXAMPLE 40

The reaction was conducted in the same manner as in Example 39 except that 0.23 ml (1.6 mmol) of trimethylsilylacetylene was used instead of 3-hexyne. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 96% |
|---|---|---|
| 3MB1 | Production ratio | 81% |
| 2MB1 | " | 3.6% |
| 2MB2 | " | 15% |
| 2MB | " | 0.4% |

EXAMPLE 41

The reaction was conducted in the same manner as in Example 39 except that 0.17 ml (1.6 mmol) of phenylacetylene was used instead of 3-hexyne. When the absorption of hydrogen reached about 90% of the theoretical amount, the reaction solution was analyzed, whereby the conversion of IP was 90%, and the production ratio of 3MB1 was 83%. The conversion of IP was further increased, and when absorption of a substantially theoretical amount of hydrogen was observed, the reaction solution was analyzed, whereby the following results were obtained.

| IP | Conversion | 96% |
|---|---|---|
| 3MB1 | Production ratio | 83% |
| 2MB1 | " | 3.7% |
| 2MB2 | " | 13% |
| 2MB | " | 0.3% |

EXAMPLE 42

The reaction was conducted in the same manner as in Example 39 except that 285 mg (1.6 mmol) of diphenylacetylene was used instead of 3-hexyne. When the absorption of hydrogen reached about 90% of the theoretical amount, the reaction solution was analyzed, whereby the conversion of IP was 90%, and the production ratio of 3MB1 was 81%. The conversion of IP was further increased, and when absorption of a substantially theoretical amount of hydrogen was observed, the reaction solution was analyzed, whereby the following results were obtained.

| IP | Conversion | 93% |
|---|---|---|
| 3MB1 | Production ratio | 81% |
| 2MB1 | " | 4.7% |
| 2MB2 | " | 14% |
| 2MB | " | 0.3% |

EXAMPLE 43

Into a flask having a capacity of 100 ml, 59 mg (0.2 mmol) of cobalt (II) acetylacetonate dihydrate and 157 mg (0.6 mmol) of triphenylphosphine were charged, and after thoroughly flushing the interior of the flask with nitrogen, 20 ml of chlorobenzene was added as a solvent. To the suspension solution of chlorobenzene, 0.60 ml (0.46 mmol) of a toluene solution containing 10.0% by weight of triethylaluminum was dropwise added under stirring and cooling with ice water. Further, 0.96 ml (0.34 mmol) of a toluene solution containing 10.0% by weight of ethylaluminum sesquichloride was dropwise added, and finally 0.39 ml (3.0 mmol) of 1-vinylcyclohexene was added. After flushing the interior of the system with hydrogen, hydrogen was introduced under atmospheric pressure while vigorously stirring and cooling with ice water. After the initiation of the introduction of hydrogen, absorption of hydrogen started. After the reaction for 20 minutes, the reaction solution was analyzed by gas chromatography, whereby the following results were obtained.

| 1-Vinylcyclohexene | Conversion | 80% |
|---|---|---|
| Vinylcyclohexene | Production ratio | 90% |
| 1-Methylcyclohexene | " | 10% |

EXAMPLE 44 reaction was conducted in the same manner as in Example 43 except that 0.51 ml (3.0 mmol) of myrcene was used instead of 1-vinylcyclohexene, and 20 ml of dichlorobenzene was used as the solvent. Upon expiration of 8 minutes from the initiation of the reaction, the reaction solution was analyzed by gas chromatography, whereby the following results were obtained.

| Myrcene | Conversion | 90% |
|---|---|---|
| 3,7-Dimethyl-octa-1,6-diene | Production ratio | 66% |
| 3,7-Dimethyl-trans-octa-2,6-diene | " | 13% |
| 3,7-Dimethyl-cis-octa-2,6-diene | " | 21% |

EXAMPLE 45

The reaction was conducted in the same manner as in Example 43 except that 38 mg (0.28 mmol) of aluminum chloride was used instead of the toluene solution of ethylaluminum sesquichloride, 0.85 ml (5.0 mmol) of myrcene was used instead of 1-vinylcyclohexene, and 20 ml of trichlorobenzene was used as the solvent. Upon expiration of 20 minutes from the initiation of the reaction, the reaction solution was analyzed by gas chromatography, whereby the following results were obtained.

| Myrcene | Conversion | 90% |
|---|---|---|
| 3,7-Dimethyl-octa-1,6-diene | Production ratio | 59% |
| 3,7-Dimethyl-trans-octa-2,6-diene | " | 27% |
| 3,7-Dimethyl-cis-octa-2,6-diene | " | 14% |

EXAMPLE 46

The reaction was conducted in the same manner as in Example 43 except that 0.3 ml (3.0 mmol) of trans-1,3-pentadiene was used instead of 1-vinylcyclohexene. Upon expiration of 11 minutes from the initiation of the reaction, the reaction solution was analyzed by gas chromatography, whereby the following results were obtained.

| trans-1,3-Pentadiene | Conversion | 92% |
|---|---|---|
| 1-Pentene | Production ratio | 64% |
| trans-2-Pentene | " | 27% |
| cis-2-Pentene | " | 9% |

EXAMPLE 47

Into a flask having a capacity of 100 ml, 59 mg (0.2 mmol) of cobalt (II) acetylacetonate dihydrate and 392 mg (0.6 mmol) of 1,1,2,2-tetramethyl-1,2-bis(p-diphenylphosphinophenyl)disiloxane were charged, and after thoroughly flushing the interior of the flask with nitrogen, 20 ml of chlorobenzene was added. To the suspension solution of chlorobenzene, 0.60 ml (0.46 mmol) of a toluene solution containing 10.0% by weight of triethylaluminum was dropwise added under stirring and cooling with ice water. Further, 0.96 ml (0.34 mmol) of a toluene solution containing 10.0% by weight of ethyl-aluminum sesquichloride was dropwise added, and finally 0.3 ml (3.0 mmol) of isoprene was added. After flushing the interior of the system with hydrogen, hydrogen was introduced under atmospheric pressure while vigorously stirring and cooling with ice water. After the initiation of the introduction of hydrogen, absorption of hydrogen started, and the hydrogenation reaction proceeded.

Upon expiration of 6 minutes from the initiation of the reaction, the absorption of hydrogen reached about 80% of the theoretical amount, whereupon the reaction solution was analyzed, whereby the following results were obtained.

| IP | Conversion | 82% |
|---|---|---|
| 3MB1 | Production ratio | 81% |
| 2MB1 | " | 2% |
| 2MB2 | " | 17% |

The hydrogenation reaction was continued, and upon expiration of 15 minutes from the initiation of the reaction, absorption of a substantially theoretical amount of hydrogen was observed, whereupon the reaction solution was analyzed, whereby the following results were obtained.

| IP | Conversion | 100% |
|---|---|---|
| 3MB1 | Production ratio | 76% |
| 2MB1 | " | 3% |
| 2MB2 | " | 21% |

EXAMPLE 48

The reaction was conducted in the same manner as in Example 47 except that 384 mg (0.3 mmol) of 1,2,3,4-tetramethyl-1,2,3,4-tetrakis(p-diphenylphosphinophenyl)cyclotetrasiloxane was used instead of 1,1,2,2-tetramethyl-1,2-bis(p-diphenylphosphinophenyl)-disiloxane. Upon expiration of 7 minutes from the initiation of the reaction, the absorption of hydrogen reached about 80% of the theoretical amount, whereupon the reaction solution was analyzed, whereby the following results were obtained.

| IP | Conversion | 82% |
|---|---|---|
| 3MB1 | Production ratio | 79% |
| 2MB1 | " | 4% |
| 2MB2 | " | 17% |

The conversion of IP was further increased, and when absorption of a substantially theoretical amount of hydrogen was observed upon expiration of 15 minutes from the initiation of the reaction, the reaction solution was analyzed, whereby the following results were obtained.

| IP | Conversion | 100% |
|---|---|---|
| 3MB1 | Production ratio | 71% |
| 2MB1 | " | 4.7% |
| 2MB2 | " | 24% |
| 2MB | " | 0.3% |

We claim:
1. A method for the partial hydrogenation of conjugated dienes, characterized in that a chain conjugated diene in which the conjugated two double bonds have different numbers of substituents, is hydrogenated at a temperature of not higher than 50° C. in the presence of a catalyst composed essentially of (1) a cobalt compound, (2) an organophosphine compound and (3) an aluminum compound, to obtain a partially hydrogenated product wherein as between said conjugated two double bonds, the one having a greater number of substituents is selectively hydrogenated.
2. The method according to claim 1, wherein the chain conjugated diene is isoprene.
3. The method according to claim 1, wherein the aluminum compound is an organoaluminum compound.
4. The method according to claim 1, wherein a boron halide compound is used as an additional catalyst component.
5. The method according to claim 1, wherein a proton acid having a pKa of at most 1 is used as an additional catalyst component.
6. The method according to claim 1, wherein an α-olefin compound represented by the formula:

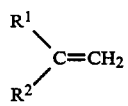

where $R^1$ is an aryl group, a tertiary alkyl group or a tertiary silyl group, and $R^2$ is a hydrogen atom, an alkyl group, a tertiary silyl group or an aryl group, is present in the reaction system.

7. The method according to claim 1, wherein a cis-olefin compound is present in the reaction system.

8. The method according to claim 1, wherein an acetylene compound is present in the reaction system.

9. The method according to claim 1, wherein the reaction is conducted at a temperature of from $-20°$ C. to $50°$ C.

10. The method according to claim 1, wherein the reaction is conducted at a temperature of from $-5°$ C. to $45°$ C.

* * * * *